United States Patent [19]
Flemming et al.

[11] Patent Number: 5,885,561
[45] Date of Patent: Mar. 23, 1999

[54] WAX COMBINATION AND COSMETIC COMPOSITIONS CONTAINING SAME

[75] Inventors: Ernst Flemming, Heusenstamm; Ursula Hehner, Brensbach; Karl-Heinz Kischka, Darmstadt; Anke Jacobs, Neckargemünd; Rudolf Bimczok, Seeheim; Bianka Schmich, Bürstadt, all of Germany

[73] Assignee: Wella Aktiengesellschaft, Darmstadt, Germany

[21] Appl. No.: 811,615

[22] Filed: Mar. 5, 1997

[30] Foreign Application Priority Data

Mar. 16, 1996 [DE] Germany .......................... 196 10 458.0
Mar. 16, 1996 [DE] Germany .......................... 196 10 459.9

[51] Int. Cl.$^6$ .................................................. A61K 7/135
[52] U.S. Cl. ........................... 424/62; 424/401; 424/70.1; 424/70.12
[58] Field of Search .................................. 424/401, 70.1, 424/70.12, 70.21, 70.22, 62

[56] References Cited

U.S. PATENT DOCUMENTS 3,929,492  12/1975  Chapman ..................................... 106/3
5,587,174  12/1996  Lang ........................................ 424/401

FOREIGN PATENT DOCUMENTS

4122591C1  2/1983  Germany .

*Primary Examiner*—Thurman K. Page
*Assistant Examiner*—D. Faulkner
*Attorney, Agent, or Firm*—Michael J. Striker

[57] ABSTRACT

The wax combination for the cosmetic compositions contains from 2 to 70 percent by weight of apple wax; from 5 to 70 percent by weight of orange wax and/or citric wax; and from 10 to 70 percent by weight of jojoba oil. The cosmetic compositions advantageously contain a portion of the wax combination in free form or an effective ingredient complex consisting of capsules, each containing some of the wax combination.

18 Claims, No Drawings

WAX COMBINATION AND COSMETIC COMPOSITIONS CONTAINING SAME

BACKGROUND OF THE INVENTION

The present invention relates to a wax composition comprising a combination of apple wax, orange wax and/or citric wax and jojoba oil and cosmetic compositions for treating skin or hair, which contains these wax combinations in free form or as a complex of effective ingredients, which is formed by enclosing a wax combination in a capsule.

Waxes can fulfill many needs in cosmetic compositions. For example, they can be used by themselves alone for covering the skin or they can be added in an emulsion for viscosity modification and stabilization of cosmetic compositions. Waxes can be used for oiling and hydrophobic treatment of the skin in domestic cosmetic compositions and for conditioning and care of the hair in hair treatment compositions.

Waxes can be divided into natural, chemically modified and synthetic waxes according to the manner in which they are manufactured. Mineral waxes, and certain natural waxes of animal and vegetable origin, are among the waxes which are of significance for cosmetic compositions.

Natural and chemically modified natural mineral waxes originate from nonrenewable raw material sources, and/or are made from raw materials derived from these sources. Synthetic mineral waxes frequently contain synthetically derived impurities.

The use of natural or chemically modified natural waxes of animal or vegetable origin avoids the aforementioned disadvantages of mineral waxes and satisfies the widespread desire in commercial circles to use natural, ecologically unobjectionable raw materials.

The best known animal wax is beeswax, whose availability as a deposition product of bees is however limited. Furthermore beeswax has a high proportion of esters, which can disadvantageously effect the stability of the beeswax-containing compositions.

The current commercially obtainable vegetable waxes used in cosmetic compositions are candelilla and carnauba wax. These waxes are however hard and brittle, have high melting points and are only emulsified with difficulty in common vegetable wax.

SUMMARY OF THE INVENTION

It has now been found that a wax combination of apple wax, orange wax and/or citric wax and jojoba oil does not have these above-mentioned disadvantages.

Furthermore cosmetic compositions using the wax combination according to the invention have a synergistic skin protecting and skin and/or hair conditioning action in comparison to individual components, e.g. apple wax as described in German Published Patent Application, DE-OS 42 06 154.

Moreover commercial cosmetic compositions have the disadvantage that not all raw materials and effective ingredients are arbitrarily combinable, since undesirable side reactions can occur between them, or they are pH sensitive. Because of that, selection of suitable ingredients and thus optimization of their action is greatly limited.

To get around these difficulties it is known to use a many chambered packaging system, but this is however expensive and involves extra effort. It is also known to enclose individual effective ingredients in gelatin capsules, but there are problems regarding easy application and distribution of the effective ingredients without forming a residue.

It has now been found that the wax combination according to the invention especially may be satisfactorily included in suitable capsules, whereby a satisfactory distribution is obtained with a wide variety of materials used in cosmetic compositions and simultaneously an easy application and distribution of the wax combination on the hair or the skin without leaving a residue is guaranteed.

The wax combination according to the invention thus comprises:

a) 0.01 to 99 percent by weight, advantageously from 2 to 70 percent by weight, apple wax;

b) 0.01 to 99 percent by weight, advantageously from 5 to 70 percent by weight, orange and/or citric wax; and c) 0.01 to 99 percent by weight, advantageously 10 to 70 percent by weight, jojoba oil.

The present invention also includes cosmetic compositions for the treatment of skin or hair, which contain the above-described wax combination either in free form or as a complex of active or effective ingredients, which is formed by enclosing portions of the wax combination in capsules.

Capsules suitable for the effective ingredient complex are made from water-insoluble polymers, especially from microcrystalline cellulose and contain hydroypropylmethylcellulose and lactose as auxiliary agents. Suitable capsules are, for example, marketed using the Unispheres process, especially Unispheres UFW-523 and Unispheres RFW-522 of Inducehm, Dübendorf, Switzerland.

A variety of processes are described in the literature for making capsules loaded with effective ingredients. The encapsulation of wax combination according to the invention can occur according to any one of these processes. These processes include chemical processes, whereby the product to be encapsulated is added to a liquid medium, in which the wall of the capsule forms around it coaservatively or the capsule wall is formed by copolymerization of the monomers contained in the liquid medium. The process can also be one of the known chemical methods of encapsulation. In these methods the substances to be encapsulated, for example in fine particles, are centrifuged, and guided by a thin film which is made from material forming the capsule wall or substance to be encapsulated is comminuted in vacuum and an electrostatic coating is deposited. A suitable process is, for example, described in German Published Patent Application DE-OS 41 22 591. An encapsulation process is particularly preferred in which the substances used together are mixed in the presence of water and the capsules are made by the rotary fluidized bed process.

An apple wax suitable for the wax combination according to the invention is sold under the trademark or tradename Apple Wax Green 2/080025® of Dragoco, Holzminden, Germany.

An orange wax suitable for the wax combination according to the invention is sold, for example, under the Trademark, Orange Peel Wax®, and a suitable citric wax under the trademark, Lemon Peel Wax®, of Koster Keunen b.v., Netherlands.

A Jojoba oil suitable for use in the wax combination according to the invention is marketed, for example, under the trademark, Jojoba oil®, of Hess GmbH, Stuttgart, Germany.

The wax combination according to the invention is made by melting the three components a), b) and c) at 50° to 60° C., using a suitable stirring apparatus and subsequent cooling.

If the wax combination for making the effective ingredient complexes is encapsulated, the capsules should contain from 0.01 to 30 percent by weight, advantageously from 0.1 to 20 percent by weight of the wax combination, relative to the capsule weight. In a cosmetic composition the effective ingredient complex should be contained in an amount of from 0.01 to 50 percent by weight, advantageously from 0.03 to 20 percent by weight. The effective ingredient may be easily applied and distributed on the hair or skin without leaving a residue and is satisfactory for making a clear gel.

The wax combination according to the invention just like the effective ingredient complex has a skin protecting action and has a weaker occlusive effect than the frequently used Vaseline® in cosmetic compositions. Both the wax combination and the effective ingredient complex are thus outstanding as ingredients of hair protecting and hair care cosmetic compositions.

The wax combination according to the invention can be used in pure form for covering and for protection of skin. As ingredients of cosmetic hair care and hair purifying agents improves the wet and dry combability of the effective ingredient complex and the feel of the hair and protects the hair prior to the action of cosmetic treatments such as bleaching, permanent wave treatments, dyeing and washing with deoiling surfactants. If the wax combination according to the invention is used in free form in a cosmetic composition, then its proportion amounts to between 0.03 to 99.8 percent by weight.

The cosmetic composition according to the invention, for example, can be a skin protecting or care composition, e.g., a day cream, a night cream, skin cream, sun screen cream, lip stick, lip care composition, or a make-up preparation, such as a cosmetic composition or rouge, such as a hair and/or body cleansing composition, such as a shampoo, douche bath, foam bath or cleaning lotion. Moreover they can be used as a hair treatment composition such as a hair oil, gel or hair wax, such as a hair care composition, e.g. as a hair care and hair rinse composition or as a bleaching agent, permanent wave composition, hair fixing composition, such as a hair dye composition or hair tinting composition.

Skin protecting or skin care compositions according to the invention contain preferably from 0.03 to 50 percent by weight of a wax combination according to the invention in a free form or from 0.02 to 15 percent by weight of the effective ingredient complex according to the invention. A skin protecting or skin care composition according to the invention in the form of an oil-in-water emulsion contains especially advantageously from 0.03 to 20 percent by weight of the wax combination according to the invention in free form.

The hair or body cleansing composition or hair care composition according to the invention preferably contains 0.05 percent by weight in free form or from 0.02 to 4 percent by weight of the effective ingredient complex. The cosmetic composition of this type moreover contains from 0.01 to 40 percent by weight of at least one anionic, cationic, amphoteric and/or nonionic surfactant as well as from 50 to 90 percent by weight of water.

The hair and/or body cleansing composition according to the invention has a pH-value of from 3 to 8, advantageously from 4 to 7. The sun screen according to the invention contains preferably from 0.1 to 80% by weight of the wax combination according to the invention in a free form or from 0.01 to 20 percent by weight of the effective ingredient complex. The hair oil, brillantinen, hair gel and hair wax according to the invention preferably contains from 1 to 99.8% by weight of the wax combination according to the invention in free form, or from 1 to 19 percent by weight of the effective ingredient complex.

The hair fixing and permanent wave composition according to the invention preferably has a content of 0.05 to 5 percent by weight of the wax combination according to the invention and contains moreover from 0.05 to 15 percent by weight of at least one keratin-reducing mercapto compound. A composition of this type is preferably present as an aqueous, alkaline (pH=5 to 10) preparation, which contains for example cysteine, cysteamine, N-acetyl-L-cysteine, mercaptocarboxylic acids, such as thioglycolic acid or thiolactic acid, or salts of mercaptocarboxylic acids, such as ammonium or guanidine salts of thioglycolic acid or thiolactic acid.

The required alkalinity or basicity is adjusted by addition of ammonia, organic amines, ammonium and alkali carbonates or hydrogen carbonates. The hair shaping composition according to the invention can also be neutral or acidic with a pH of 4.5 to 7 and has an effective content of sulfites or mercaptocarboxylic acid esters in aqueous medium.

In the first case preferably sodium or ammonium sulfite or the salts of sulfuric acid are used with an organic amine, such as monoethanolamine and guanidine, in a concentration of about 2 to 12 percent by weight(calculated as $SO_2$). In the latter case, especially thioglycolic acid monoglycolic ester or glycerin ester is used in a concentration of about 5 to 50 percent by weight (suitably a content of free thioglycolic acid of 2 to 16 percent by weight).

The composition for permanent shaping of hair according to the invention can contain a mixture of the above-described keratin-reducing compounds.

After an acting time sufficient for the permanent shaping of hair, which, according to the nature of the hair, the pH and the shaping action of the hair shaping agent and according to the application temperature, amounts to about 10 to 30 minutes, the hair is rinsed with water and subsequently oxidatively after-treated (i.e. "fixed"). The after treatment composition is, according to the amount of hair, used in an amount of from about 50 to 100 g.

For the oxidative after-treatment a fixing agent according to the invention or any arbitrary fixing agent can be used for this type of treatment. For example, oxidizing compositions usable in this type of fixing composition include sodium and potassium bromate, sodium perborate, urea peroxide and hydrogen peroxide.

The concentration of oxidizing agent differs according to the application time (in an amount of about 5 to 15 minutes) and the application temperature. Usually the oxidizing agent is present in the aqueous fixing agent in a concentration of about 0.5 to 10 percent by weight. The fixing composition according to the invention contains also from 0.05 to 5 percent by weight of the wax combination according to the invention.

Both the composition according to the invention for permanent shaping of hair and the hair fixing composition according to the invention can be in the form of an aqueous solution or emulsion and in thickened form on an aqueous basis, especially as a cream, gel or paste. Similarly it is also possible to fill this composition under pressure into an aerosol can and to dispense it as a foam.

Subsequently the curlers used in the permanent wave treatment are removed. As the case may require, the curled hair can then be subjected to an oxidative after-treatment. Then the hair is rinsed with water, set in a hair-do and subsequently dried.

The above-described method for permanent shaping of hair provides a safe and uniform shaping from the hair roots to the hair tips, an outstanding wet and dry hair combability, a pleasant feel and a pleasing look in the dry state. A more attractive, springy and uniform permanent shaping of the hair is provided, especially in the vicinity of the hair tips.

A bleaching agent, oxidation hair dye composition or hair tinting composition according to the invention contains advantageously from 0.05 to 5% by weight of the wax combination according to the invention or the effective ingredient complex.

The hair tinting agent according to the invention contains additionally to the wax combination according to the invention from 0.05 to 2.0 percent by weight of at least one direct dyeing hair dye compound, which can be selected for example from the following classes of direct dye compounds: aromatic nitro dye compounds, e.g. 1,4-diamino-2-nitrobenzene, azo dye compounds, e.g. Acid Brown 4 (C.I. 14 805), anthraquinone dye compounds, such as Disperse Violet 4(C.I. 61 105), and triphenylmethane dye compounds, e.g. Basic Violet 1 (C.I. 42 535). These direct dyeing dye compounds can have a neutral, acidic or basic character according to their substituents, such as Henna and Reng, which do not require oxidation to develop color.

The compositions according to the invention can be in any preparation form suitable for skin and hair treatment composition, e.g. in the form of an aqueous-alcoholic or alcoholic solution, such as an emulsion, a cream or a gel. The composition according to the invention, in a mixture with a propellant gas, can be sprayed or foamed or can be sprayed by means of a mechanically driven spraying device.

When the composition according to the invention is sprayed with the aid of a propellant, it preferably contains from 3 to 75 percent by weight of the propellant and is filled in a pressurized container.

Lower alkanes, such as n-butane, i-butane and propane, or their mixtures with dimethyl ether are, for example, suitable as propellants. Gases, such as $N_2$, $N_2O$ and $CO_2$, and mixtures thereof are also suitable as propellants.

"Mechanical spraying devices or apparatus" are to be understood here to be devices which will spray liquids without using a propellant. For example, an elastic container provided with a spray pump or an elastic container provided with a spray valve, in which the cosmetic composition according to the invention is filled under pressure so that the elastic container expands and from which the composition can be delivered continuously on contraction of the elastic container on opening of the spray valve, is suitable as a mechanical spraying device.

The cosmetic composition according to the invention can also include conventional cosmetic ingredients for hair and skin treatment compositions, for example, solvents, such as water and lower aliphatic alcohols, such as ethanol, propanol and isopropanol, or glycols, such as glycerol and 1,2-propylene glycol; wetting agents and emulsifiers from the classes of anionic, cationic, amphoteric or nonionic surfactants, such as fatty alcohol sulfates, alkylbenzenesulfonates, alklytrimethylammonium salts, alkylbetaine, ethoxylated fatty alcohols, ethoxylated nonylphenols, fatty acid alkanolamides, ethoxylated fatty acid esters, in amount of from 0.1 to 30 percent by weight; perfume oils, in an amount of from 0.5 to 5% by weight; turbidity inducing agents, such as ethyleneglycoldistearate, in an amount of from about 0.5 to 5.0 percent by weight; pearlescent agents, such as a mixture of fatty acid monoalkylolamides and ethyleneglycoldistearates, in an amount of from about 1.0 to 10 percent by weight; bactericide and fungicide ingredients, for example 2,4,4-trichloro-2-hydroxydiphenylether or methylchloroisothiazolinone, in amounts of from 0.01 to 1.0 percent by weight; thickening agents, such as coconut oil fatty acid diethanolamides, in an amount of about 0.5 to 3.0 percent by weight; buffer substances, such as sodium citrate or sodium phosphate, in an amount of 0.1 to 1.0 percent by weight; solvating agents, such as ethoxylated castor oil, in an amount of about 0.1 to 1.0 percent by weight; dye compounds, for example fluorescein sodium salts, in an amount of about 0.1 to 1.0 percent by weight; hair care materials, for example cationic resin, lanolin derivatives, in an amount of 0.1 to 5 percent by weight; light protecting agents, moisturizers, antioxidants, complex formers and antiflaking agents in an amount of about 0.01 to 0.8 percent by weight as well as additional physiologically compatible organic acids, such as formic acid, glyoxylic acid, lactic acid, tartaric acid, citric acid; natural, modified natural or synthetic polymers, such as shellac; cationic, anionic nonionic or amphoteric polymers, chitosan, chitin or chitosan derivatives.

The subject matter of the invention is illustrated further by the following examples, which are not intended to limit the scope of any of the appended claims.

EXAMPLES

Example 1

Wax Combination

| | |
|---|---|
| 15 g | apple wax |
| 45 g | orange wax |
| 40 g | jojoba oil |
| 100 g | |

Example 2

Wax Combination

| | |
|---|---|
| 8 g | apple wax |
| 40 g | citric wax |
| 50 g | jojoba oil |
| 100 g | |

Example 3

Wax Combination

| | |
|---|---|
| 20 g | apple wax |
| 30 g | citric wax |
| 50 g | jojoba oil |
| 100 g | |

Example 4

Wax Combination

| | |
|---|---|
| 12 g | apple wax |
| 48 g | citric wax |
| 40 g | jojoba oil |
| 100 g | |

Example 5
Skin Cream with Protective Action

| | |
|---|---|
| 2.00 g | wax combination according to Example 1 |
| 8.30 g | glycerin stearate, self-emulsifying |
| 1.70 g | of a mixture of glyceryl hydroxystearate, cetylpalmitate, microcrystalline wax and trihydroxystearin (Cutina BW ®, Henkel KGAA) |
| 1.50 g | stearin |
| 7.50 g | liquid paraffin |
| 0.10 g | p-hydroxybenzoic acid propyl ester |
| 0.30 g | p-hydroxybenzoic acid methyl ester |
| 0.10 g | allantoin |
| 0.20 g | perfume oil |
| 78.30 g | water, desalinized |
| 100.0 g | |

Example 6
Skin Cream with Protective Action

| | |
|---|---|
| 4.50 g | wax combination according to Example 2 |
| 7.00 g | glycerin stearate, self-emulsifying |
| 1.40 g | stearin |
| 7.60 g | liquid paraffin |
| 0.10 g | p-hydroxybenzoic acid propyl ester |
| 0.30 g | p-hydroxybenzoic acid methyl ester |
| 0.10 g | allantoin |
| 0.20 g | perfume oil |
| 78.80 g | water, desalinized |
| 100.0 g | |

Example 7
Lip Care Stick

| | |
|---|---|
| 26.00 g | castor oil |
| 4.00 g | babassu oil |
| 19.00 g | mineral oil |
| 28.00 g | microcrystalline wax (Lunacera ® M) |
| 14.00 g | decyloleate |
| 7.00 g | wax combination according to example 2 |
| 2.00 g | water, desalinized |
| 100.00 g | |

Example 8
Sun Protective Cream (Oil-in-Water Emulsion)

| | |
|---|---|
| 7.00 g | glyceryl stearate |
| 2.50 g | cetylstearyl alcohol |
| 1.80 g | cetylstearyl alcohol ethoxylated with 20 Mol ethylene oxide |
| 1.40 g | cetylstearyl alcohol ethoxylated with 12 Mol ethylene oxide |
| 3.20 g | wax combination according to example 1 |
| 6.50 g | mixed triesters of glycerol with capric acid and caprylic acid |
| 7.50 g | mixtures of esters of capric and caprylic acid with coconut oil alcohol |
| 6.20 g | dibutyladipate |
| 3.80 g | octyldodecanol |
| 2.50 g | dimethylpolysiloxane |
| 3.80 g | 4-methoxycinnamic acid 2-ethylhexyl ester |
| 2.70 g | glycerol |
| 51.10 g | water, desalinized |
| 100.0 g | |

Example 9
Shampoo

| | |
|---|---|
| 2.744 g | sodium lauryl ether sulfate |
| 0.029 g | benzoic acid |
| 1.500 g | coconut oil fatty acid amidopropyl betaine |
| 2.000 g | ethyleneglycoldistearate |
| 0.400 g | wax combination according to example 3 |
| 0.400 g | perfume oil |
| 3.300 g | sodium chloride |
| 89.627 g | water, desalinized |
| 100.00 g | |

Example 10
Hair Care Rinse

| | |
|---|---|
| 3.50 g | cetylstearyl alcohol |
| 0.50 g | wax combination according to example 4 |
| 0.60 g | cetyltrimethylammonium chloride |
| 0.40 g | citric acid |
| 0.40 g | perfume oil |
| 94.60 g | water, deionized water |
| 100.00 g | |

Example 11
Hair Care Rinse

| | |
|---|---|
| 2.50 g | cetylstearyl alcohol |
| 0.80 g | laurylalcoholdiglycolether |
| 1.10 g | Vaseline ® |
| 1.20 g | wax combination according to example 4 |
| 0.40 g | cetylstearyl sulfate-sodium salt |
| 5.00 g | betaine monohydrate |
| 0.20 g | benzoic acid |
| 0.80 g | glyoxylic acid |
| 0.20 g | perfume oil |
| 87.80 g | water, deionized |
| 100.00 g | |

Example 12
Rinsable Hair Care Foam

| | |
|---|---|
| 0.40 g | wax combination according to example 4 |
| 10.00 g | ethanol |
| 0.30 g | polyoxyethyleneglycol derivative of castor oil (CTFA: PEG-35 castor oil) |
| 0.30 g | polyethyleneglycol(4)lauryl ether |
| 0.10 g | cetyltrimethylammonium chloride |
| 0.07 g | isopropanol |
| 1.40 g | vinylimidazoliniummethochloride/ vinylpyrrolidone copolymer (CTFA: Polyquaternum-16) |
| 0.30 g | perfume oil |
| 87.13 g | water |
| 100.00 g | |

96 g of the above-mentioned hair care composition are filled into an aerosol container with 4 g of a mixture which is 50 percent by weight propane and 50 percent by weight n-butane. On spraying the hair care composition according to the invention leaves the container in the form of a foam.

Example 13
Hair Care Composition, nonrinsable

| | |
|---|---|
| 0.100 g | wax composition according to example 3 |
| 0.112 g | isopropanol |
| 0.600 g | distearyldimethylammonium chloride |
| 0.200 g | glyceryl monostearate |
| 0.150 g | polyoxyethylen-45-polyoxypropylen-33-monobutylether |
| 0.100 g | stearyl alcohol |
| 0.090 g | stearyl betaine |
| 0.100 g | p-hydroxybenzoic acid methyl ester |
| 0.840 g | ethanol |
| 97.708 g | water |
| 100.00 g | |

Example 14
Hair Styling Gel

| | |
|---|---|
| 0.10 g | wax combination of Example 3 |
| 3.00 g | polyvinyl pyrrolidone |
| 0.50 g | polyacrylic acid (CTFA: carbomer) |
| 12.00 g | ethanol |
| 0.10 g | ammonia |
| 84.30 g | water |
| 100.00 g | |

Example 15
Hair Spray

| | |
|---|---|
| 0.20 g | wax combination according to example 1 |
| 5.00 g | polyvinylpyrrolidone/vinylacetate copolymer |
| 0.20 g | perfume oil |
| 60.00 g | n-butane |
| 34.60 g | ethanol |
| 100.00 g | |

Example 16
Sprayable Hair Care Composition, nonrinsable

| | |
|---|---|
| 0.30 g | wax combination according to example 2 |
| 0.10 g | keratin hydrolyzate |
| 0.40 g | cetyltrimethylammonium chloride |
| 0.28 g | isopropanol |
| 0.33 g | coconut oil fatty acid amidopropylbetaine |
| 0.90 g | polyvinylpyrrolidone |
| 0.20 g | citric acid |
| 97.49 g | water |
| 100.00 g | |

Example 17
Sprayable Hair Care Composition, nonrinsable

| | |
|---|---|
| 0.20 g | wax combination according to example 2 |
| 0.80 g | polyvinylpyrrolidone |
| 0.32 g | vinylimidazolinium methochloride/vinylpyrrolidone copolymer |
| 0.21 g | coconut fatty acid amidopropyl betaine |
| 0.05 g | hydrogenated castor oil derivative with 7 Mol polyethylene glycol; (CTFA: PEG-7-hydrogenated castor oil) |
| 0.18 g | hydrogenated castor oil derivative with 40 Mol polyethylene glycol; (CTFA: PEG-40-hydrogenated castor oil) |
| 0.20 g | keratin hydrolyzate |
| 12.00 g | ethanol |
| 0.20 g | glyoxylic acid |
| 85.84 g | water |
| 100.00 g | |

Example 18
Permanent Wave Shaping Composition

| | |
|---|---|
| 0.15 g | wax combination according to Example 2 |
| 8.82 g | thioglycolic acid |
| 0.90 g | castor oil derivative with 35 Mol polyethylene glycol; (CTFA: PEG-35-castor oil) |
| 0.90 g | polyethyleneglycol-23-nonylphenol ether |
| 0.90 g | poly(diallyldimethylammonium chloride) |
| 0.28 g | styrene/polyvinylpyrrolidone copolymer |
| 0.15 g | ammonia |
| 3.50 g | ammonium hydrogen carbonate |
| 0.50 g | perfume oil |
| 83.90 g | water |
| 100.00 g | |

Example 19
Fixing Composition for Permanent Shaping (Neutralizing Agent)

| | |
|---|---|
| 0.200 g | wax combination according to example 1 |
| 2.610 g | cetylstearyl alcohol |
| 0.290 g | sodium lauryl sulfate |
| 0.400 g | lanolin alcohol |
| 1.900 g | hydrogen peroxide |
| 0.085 g | phosphoric acid |
| 0.100 g | salicylic acid |
| 0.300 g | perfume oil |
| 94.115 g | water |
| 100.00 g | |

Example 20
Hair Tinting Composition

| | |
|---|---|
| 0.200 g | wax combination according to example 3 |
| 4.500 g | cetylstearyl alcohol |
| 1.750 g | cetyltrimethylammonium chloride |
| 4.2250 g | isopropanol |
| 0.0025 g | Basic violet 14 (C.I. Nr. 42,510) |
| 89.322 g | water |
| 100.00 g | |

94.00 g of the above-mentioned hair tinting foam are filled into an aerosol container with 6 g of a mixture of 50 percent by weight propane, 40 percent by weight n-butane and 10 percent by weight dimethylether.

Example 21
Oxidative Hair Dye Composition (Dark brown)

| | |
|---|---|
| 0.60 g | wax combination according to Example 2 |
| 17.10 g | cetylstearyl alcohol |
| 1.90 g | sodium lauryl sulfate |
| 2.10 g | lanolin alcohol |
| 6.10 g | glycerylstearate, self-emulsifying |
| 0.40 g | sodium salt of coconut fatty acid ester of isoethionic acid (CTFA: sodium cocoylisoethionate) |
| 1.40 g | sodium lauryl ether sulfate |
| 0.06 g | p-aminophenol hydrochloride |
| 0.65 g | p-toluylenediaminesulfate |
| 0.26 g | resorcinol |
| 0.60 g | sodium sulfite |
| 0.30 g | ethylenediaminetetracetic acid |
| 6.00 g | isopropanol |
| 0.30 g | perfume oil |
| 1.40 g | ammonia |
| 60.83 g | water |
| 100.00 g | |

Prior to application 50 g of the above-described oxidative hair dye composition are mixed with 50 ml of hydrogen peroxide (6% aqueous solution).

Example 22
Effective Ingredient Complex

| | |
|---|---|
| 15 g | apple wax |
| 45 g | orange wax |
| 40 g | jojoba oil |
| 100 g, | | enclosed in 1.000 g capsules made from cellulose, hydroxypropylmethylcellulose and lactose (Unispheres of Inducehm/Dübendorf, Switzerland).

Example 23
Effective Ingredient Complex

| | |
|---|---|
| 8 g | apple wax |
| 40 g | orange wax |
| 52 g | jojoba oil |
| 100 g, | | enclosed in 0.500 g capsules made from cellulose, hydroxypropylmethylcellulose and lactose (Unispheres of Inducehm/Dübendorf, Switzerland).

Example 24
Effective Ingredient Complex

| | |
|---|---|
| 20 g | apple wax |
| 30 g | citric wax |
| 50 g | jojoba oil |
| 100 g, | | enclosed in 0.770 g capsules made from cellulose, hydroxypropylmethylcellulose and lactose (Unispheres of Inducehm/Dübendorf, Switzerland).

Example 25
Effective Ingredient Complex

| | |
|---|---|
| 12 g | apple wax |
| 48 g | citric wax |
| 40 g | jojoba oil |
| 100 g, | | enclosed in 0.556 capsules made from cellulose, hydroxypropylmethylcellulose and lactose (Unispheres of Inducehm/Dübendorf, Switzerland).

Example 26
Skin Cream with Protective Action

| | |
|---|---|
| 10.00 g | Effective Ingredient Complex according to example 22 |
| 8.30 g | glyceryl stearate, self-emulsifying |
| 1.70 g | of a mixture of glyceryl hydroxystearate, cetyl palmitate, microcrystalline wax and trihydroxystearin |
| 1.50 g | stearin |
| 7.50 g | liquid paraffin |
| 0.10 g | p-hydroxybenzoic acid propyl ester |
| 0.30 g | p-hydroxybenzoic acid methyl ester |
| 0.10 g | allantoin |
| 0.20 g | perfume oil |
| 70.30 g | water, desalinized |
| 100.00 g | |

Example 27
Skin Cream with Protective Action

| | |
|---|---|
| 12.00 g | effective ingredient complex according to example 25 |
| 7.00 g | glyceryl stearate, self-emulsifying |
| 1.40 g | stearin |
| 7.60 g | liquid paraffin |
| 0.10 g | p-hydroxybenzoic acid propyl ester |
| 0.30 g | p-hydroxybenzoic acid methyl ester |
| 0.10 g | allantoin |
| 0.20 g | perfume oil |
| 71.30 g | water, desalinized |
| 100.00 g | |

Example 28
Sun Protective Cream (Oil-in-Water Emulsion)

| | |
|---|---|
| 7.00 g | glyceryl stearate |
| 2.50 g | cetylstearyl alcohol |
| 1.80 g | cetylstearyl alcohol ethoxylated with 20 Mol ethylene oxide |
| 1.40 g | cetylstearyl alcohol ethoxylated with 12 Mol ethylene oxide |
| 8.00 g | effective ingredient complex as in Example 22 |
| 6.50 g | mixed triesters of glycerol with capric acid and caprylic acid |
| 7.50 g | mixtures of esters of capric and caprylic acid with coconut oil alcohol |
| 6.20 g | dibutyladipate |
| 3.80 g | octyldodecanol |
| 2.50 g | dimethylpolysiloxane |
| 3.80 g | 4-methoxycinnamic acid 2-ethylhexyl ester |
| 2.70 g | glycerol |
| 46.30 g | water, desalinized |

-continued 100.0 g

Example 29
Shampoo

| | |
|---|---|
| 2.74 g | sodium lauryl ether sulfate |
| 0.03 g | benzoic acid |
| 1.50 g | coconut oil fatty acid amidopropyl betaine |
| 2.00 g | ethyleneglycoldistearate |
| 0.80 g | effective ingredient complex as in example 24 |
| 3.30 g | sodium chloride |
| 89.23 g | water, desalinized |
| 100.00 g | |

Example 30
Hair Care Rinse

| | |
|---|---|
| 3.50 g | cetylstearyl alcohol |
| 0.70 g | effective ingredient complex as in example 25 |
| 0.60 g | cetyltrimethylammonium chloride |
| 0.40 g | citric acid |
| 0.40 g | perfume oil |
| 94.60 g | water, deionized water |
| 100.00 g | |

Example 31
Hair Care Rinse

| | |
|---|---|
| 2.50 g | cetylstearyl alcohol |
| 0.80 g | laurylalcoholdiglycolether |
| 1.10 g | Vaseline ® |
| 1.20 g | effective ingredient complex as in example 25 |
| 0.40 g | cetylstearyl sulfate-sodium salt |
| 5.00 g | betaine monohydrate |
| 0.20 g | benzoic acid |
| 0.80 g | glyoxylic acid |
| 0.20 g | perfume oil |
| 87.80 g | water, deionized |
| 100.00 g | |

Example 32
Nonrinsable Hair Care Foam

| | |
|---|---|
| 0.50 g | efective ingredient complex as in example 23 |
| 0.50 g | polyacrylic acid |
| 0.40 g | 2-amino-2-methyl-1-propanol |
| 0.10 g | vinylpyrrolidone/dimethylaminoethyl-methacrylate copolymer |
| 0.20 g | hydrogenated castor oil, ethoxylated with 45 Mol ethylene oxide |
| 0.25 g | D-panthenol |
| 0.05 g | laurylpolyglucose |
| 12.00 g | ethanol |
| 86.00 g | water |
| 100.00 g | |

Example 33
Hair Styling Gel

| | |
|---|---|
| 0.80 g | effective ingredient complex according to example 24 |
| 3.00 g | Polyvinylpyrrolidone |
| 0.50 g | polyacrylic acid (CFTA: Carbomer) |
| 12.00 g | ethanol |
| 0.20 g | perfume oil |
| 0.10 g | ammonia |
| 83.40 g | water |
| 100.00 g | |

Example 34
Nonrinsable Hair Care Composition

| | |
|---|---|
| 0.70 g | effective ingredient complex according to example 23 |
| 0.10 g | keratin hydrolyzate |
| 0.40 g | cetyltrimethylammonium chloride |
| 0.28 g | isopropanol |
| 0.33 g | coconut fatty acid amidopropylbetaine |
| 0.90 g | polyvinylpyrrolidone |
| 0.20 g | citric acid |
| 97.09 g | water |
| 100.00 g | |

Example 35
Nonrinsable Hair Care Composition

| | |
|---|---|
| 0.80 g | Effective ingredient Complex as in Example 22 |
| 0.80 g | polyvinylpyrrolidone |
| 0.32 g | vinylimidazoliniummethochloride/vinylpyrrolidone copolymer |
| 0.21 g | coconut fatty acid amidopropylbetaine |
| 0.20 g | keratin hydrolyzate |
| 12.00 g | ethanol |
| 0.20 g | glyoxylic acid |
| 85.47 g | water |
| 100.00 g | |

Example 36
Permanent Shaping Composition

| | |
|---|---|
| 0.70 g | effective ingredient complex according to example 23 |
| 8.82 g | thioglycolic acid |
| 0.90 g | castor oil derivative with 35 Mol polyethylene glycol; (CTFA: PEG-35-castor oil) |
| 0.90 g | polyethyleneglycol-23-nonylphenol ether |
| 0.90 g | poly(diallyldimethylammonium chloride) |
| 0.28 g | styrene/polyvinylpyrrolidone copolymer |
| 0.15 g | ammonia |
| 3.50 g | ammonium hydrogen carbonate |
| 0.50 g | perfume oil |
| 83.50 g | water |
| 100.00 g | |

Example 37
Fixing Composition for Permanent Shaping (Neutralizing Agent)

| | |
|---|---|
| 1.100 g | effective ingredient complex as in Example 22 |
| 2.610 g | cetylstearyl alcohol |
| 0.290 g | sodium lauryl sulfate |
| 0.400 g | lanolin alcohol |
| 1.900 g | hydrogen peroxide |
| 0.085 g | phosphoric acid |
| 0.100 g | salicylic acid |
| 0.300 g | perfume oil |
| 93.215 g | water |
| 100.00 g | |

Example 38
Hair Tinting Agent

| | |
|---|---|
| 0.6000 g | Effective Ingredient Complex according to Example 24 |
| 4.5000 g | cetylstearyl alcohol |
| 1.7500 g | cetyltrimethylammonium chloride |
| 4.2250 g | isopropanol |
| 0.0025 g | Basic Violet 14 (C.I. Nr. 42,510) |
| 88.9225 g | water |
| 100.00 g | |

Example 39
Oxidative Hair Dye Composition(Dark brown)

| | |
|---|---|
| 0.80 g | effective ingredient complex as in Example 23 |
| 17.10 g | cetylstearyl alcohol |
| 1.90 g | sodium lauryl sulfate |
| 2.10 g | lanolin alcohol |
| 6.10 g | glycerylstearate, self-emulsifying |
| 0.40 g | sodium salt of coconut fatty acid ester of isoethionic acid (CTFA: sodium cocoylisoethionate) |
| 1.40 g | sodium lauryl ether sulfate |
| 1.40 g | ammonia |
| 0.06 g | p-aminophenol hydrochloride |
| 0.65 g | p-toluylenediaminesulfate |
| 0.26 g | resorcinol |
| 0.60 g | sodium sulfite |
| 0.30 g | ethylenediaminetetracetic acid |
| 6.00 g | isopropanol |
| 0.30 g | perfume oil |
| 60.83 g | water |
| 100.00 g | |

Prior to application 50 g of the above-described oxidative hair dye composition are mixed with 50 ml of hydrogen peroxide (6% aqueous solution).

Unless otherwise indicated all percentages are percentages by weight.

While the invention has been illustrated and described as embodied in wax compositions and cosmetic compositions containing same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

What is claimed is:

1. A cosmetic composition for treating at least one of skin and hair, said cosmetic composition containing a wax combination (as defined in claim 1) in free form said wax combination consisting of from 2 to 70 percent by weight of apple wax: from 5 to 70 percent by weight of citric wax and from 10 to 70 percent by weight of jojoba oil.

2. A cosmetic composition for treating at least one of skin and hair, said cosmetic composition containing an effective ingredient complex consisting of a plurality of capsules, each of said capsules enclosing a portion of a wax combination of from 0.01 to 99 percent by weight of apple wax. from 0.01 to 99 percent by weight of citric wax and from 0.01 to 99 percent by weight of jojoba oil.

3. The cosmetic composition as defined in claim 2, wherein each of said capsules consists of a water insoluble polymer completely enclosing from 0.01 to 30 percent by weight of said wax combination as.

4. The cosmetic composition as defined in claim 3, wherein each of said capsules contain from 0.1 to 20 percent by weight of said wax combination and said water insoluble polymer comprises microcrystalline cellulose with hydroxypropylcellulose and lactose as auxiliary materials.

5. The cosmetic composition as defined in claim 2, containing from 0.01 to 50 percent by weight of said effective ingredient complex.

6. The cosmetic composition as defined in claim 2, containing from 0.03 to 20 percent by weight of said effective ingredient complex.

7. The cosmetic composition as defined in claim 1, containing from 0.03 to 50 percent by weight of said wax combination and in the form of an emulsion for protecting skin or hair.

8. The cosmetic composition as defined in claim 2, containing from 0.02 to 15 percent by weight of said effective ingredient complex and in the form of an emulsion for protecting skin or hair.

9. The cosmetic composition as defined in claim 1, containing from 0.05 to 5 percent by weight of said wax combination and in the form of a hair care composition.

10. The cosmetic composition as defined in claim 2, containing from 0.02 to 4 percent by weight of said effective ingredient complex and in the form of a hair care composition.

11. The cosmetic composition as defined in claim 1, containing from 0.05 to 5 percent by weight of said wax combination; from 0.01 to 40 percent by weight of at least one surface-active ingredient selected from the group consisting of anionic, cationic, amphoteric and nonionic surfactants; from 50 to 90 percent by weight water; and in the form of a hair and/or body cleansing composition.

12. The cosmetic composition as defined in claim 11 and containing at least two of said surfactants.

13. The cosmetic composition as defined in claim 2, containing from 0.02 to 4 percent by weight of said effective ingredient complex; from 0.01 to 40 percent by weight of at least one surface-active ingredient selected from the group consisting of anionic, cationic, amphoteric and nonionic surfactants; from 50 to 90 percent by weight water; and in the form of a hair and/or body cleansing composition.

14. A cosmetic composition for treating at least one of skin and hair, containing from 0.05 to 5 percent by weight of a wax combination; from 0.5 to 15 percent by weight of at least on keratin-reducing mercapto compound; and in the form of an agent for permanent shaping of hair; wherein said wax combination consists of from 0.01 to 99 percent by weight of apple wax, from 0.01 to 99 percent by weight of citric wax and from 0.01 to 99 percent by weight of jojoba oil.

15. The cosmetic composition as defined in claim 2, containing from 0.05 to 5 percent by weight of said effective ingredient complex; from 0.5 to 15 percent by weight of at least one keratin-reducing mercapto compound; and in the form of an agent for permanent shaping of hair.

16. The cosmetic composition as defined in claim 1, containing from 0.05 to 5 percent by weight of said wax combination and in the form of a bleaching agent, an oxidation hair dye composition or a hair tinting composition.

17. The cosmetic composition as defined in claim 2, containing from 0.05 to 5 percent by weight of said effective ingredient complex and in the form of a bleaching agent, an oxidation hair dye composition or a hair tinting composition.

18. The cosmetic composition as defined in claim 17, further comprising from 0.05 to 2 percent by weight of at least one hair dyeing agent selected from the group consisting of natural hair dye compounds and direct dyeing hair dye compounds, and in the form of said hair tinting agent.

* * * * *